United States Patent [19]

Buschmann et al.

[11] 4,360,465
[45] Nov. 23, 1982

[54] N-ALLYL PYRROLIDINIUM SALT OF α-AMINOACETANILIDES

[75] Inventors: Ernst Buschmann, Ludwigshafen; Ulrich Schirmer, Heidelberg; Bernd Zeeh; Hubert Sauter, both of Ludwigshafen; Johann Jung, Limburgerhof, all of Fed. Rep. of Germany

[73] Assignee: BASF Aktiengesellschaft, Fed. Rep. of Germany

[21] Appl. No.: 133,241

[22] Filed: Mar. 24, 1980

[30] Foreign Application Priority Data

Apr. 14, 1979 [DE] Fed. Rep. of Germany ....... 2915250

[51] Int. Cl.$^3$ ............................................ C07D 207/09
[52] U.S. Cl. ....................................... 548/568; 71/88; 71/95; 544/58.1; 544/107; 546/290; 564/182

[58] Field of Search ................... 260/326.5 J, 326.5 L, 260/326.43

[56] References Cited

U.S. PATENT DOCUMENTS 3,014,046 12/1961 Speziale ........................... 260/347.3

FOREIGN PATENT DOCUMENTS 2657728 7/1977 Fed. Rep. of Germany .

Primary Examiner—David B. Springer
Attorney, Agent, or Firm—Keil & Witherspoon

[57] ABSTRACT

New, quaternary ammonium salts of α-aminoacetanilides of secondary anilines having a good biological action, agents for regulating plant growth containing these ammonium salts, and the use of α-aminoacetanilides of secondary anilines for manufacturing the new salts.

2 Claims, No Drawings

N-ALLYL PYRROLIDINIUM SALT OF α-AMINOACETANILIDES

The present invention relates to new, quaternary ammonium salts of α-aminoacetanilides of secondary anilines having a good biological action, agents for regulating plant growth containing these ammonium salts, and the use of α-aminoacetanilides of secondary anilines for manufacturing the new salts.

It has been disclosed (German Laid-Open Application DE-OS No. 2,657,728) that quaternary ammonium salts of α-aminoacetanilides of primary anilines of the formula

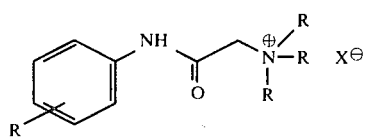

influence plant growth.

It has also been disclosed that the structural element ArNHCOR is of essential importance in photosynthesis-inhibiting arylureas, anilides and N-arylcarbamates. The transition from derivatives of primary anilines to derivatives of secondary anilines (structural element ArNalkylCOR) always results in a decrease in or blockage of biological activity (A. Barth and H.-J. Michel, Pharmazie, 24, 11-23, 1969, N. D. Camper and D. E. Moreland, Biochim. Biophys. Acta, 94, 383, 1965, and N. E. Good, Plant Physiology, 36, 788, 1961).

We have now found, surprisingly, that the new quaternary ammonium salts of α-aminoacetanilides of secondary anilines of the formula

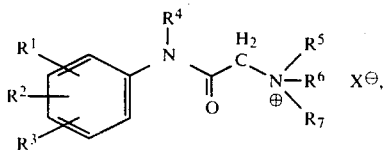

where $R^1$, $R^2$ and $R^3$ are identical or different and each denotes hydrogen, alkyl (e.g., methyl, ethyl, isopropyl), cycloalkyl, aralkyl, alkoxy (e.g., methoxy), it being possible for two adjacent radicals to form a heterocyclic ring with 1 or 2 oxygen atoms, each of $R^1$, $R^2$ and $R^3$ further denotes halogen (e.g., Br, Cl, F), haloalkyl (e.g., $CF_3$, $CF_2Cl$), $NO_2$, acyl, alkoxyalkyl, haloalkoxy, alkylthio, haloalkylthio, aryl, thiocyanato, cyano, or NHCOR', NHCONR'R'', COOR', CONR'R'', $SO_2R'$, or $SO_2NR'R''$, R' and R'' being identical or different and each denoting hydrogen, alkyl, cycloalkyl, aryl or aralkyl, $R^4$ denotes alkyl (e.g., methyl, ethyl, propyl, butyl, isobutyl), aralkyl (e.g., benzyl), alkenyl (e.g., allyl, crotyl), or alkynyl (e.g., propargyl), it being possible for the alkyl to be attached to the o-position of the aromatic ring, $R^5$, $R^6$ and $R^7$ are identical or different and each denotes alkyl, alkenyl, alkynyl, cyanoalkyl, haloalkyl, hydroxyalkyl or alkoxyalkyl, it being possible for 2 alkyls also to form, with the nitrogen atom whose substituents they are, a heterocyclic ring (e.g., pyrrolidine, piperidine, hexamethylenimine) which may contain a double bond (e.g., 1,2,5,6-tetrahydropyrimidine) or an oxygen or sulfur atom (e.g., morpholine, thiomorpholine) and be substituted by hydroxy, alkoxy, hydroxymethylene, alkoxymethylene or alkyl, and $X^\ominus$ denotes the anion of any non-phytotoxic acid (e.g., $Cl^\ominus$, $Br^\ominus$, $NO_3^\ominus$, $CH_3OSO_3^\ominus$, $CF_3SO_3^\ominus$), influence plant growth and are surprisingly superior in their growth-regulating action to the derivatives of primary anilines of the formula III described in German Laid-Open Application DE-OS No. 2,657,728.

$R^1$, $R^2$ and $R^3$ denote, independently of each other, for example hydrogen, fluorine, chlorine, bromine, iodine, trifluoromethyl, trichloromethyl, difluorochloromethyl, methoxy, ethoxy, propoxy, $NO_2$, methyl, ethyl, propyl, isopropyl, tert-butyl, benzyl, 4-chlorobenzyl, 2,4-chlorobenzyl, cyclopentyl, cyclohexyl, cycloheptyl, acetyl, propionyl, butyryl, isobutyryl, benzoyl, methoxymethyl, ethoxymethyl, trifluoromethoxy, thiomethyl, thioethyl, thioisobutyl, phenyl, 4-chlorophenyl, CN, $NHCOCH_3$, $NHCONHCH_3$, $NHCON(CH_3)_2$, $CO_2Me$ and $CO_2Et$.

Examples of meanings for $R^4$ are methyl, ethyl, propyl, isopropyl, butyl, isobutyl, allyl, crotyl, prenyl, isoprenyl, propargyl, 2-butynyl and benzyl.

$R^5$, $R^6$ and $R^7$ denote, independently of each other, for example methyl, ethyl, propyl, butyl, isobutyl, allyl, crotyl, prenyl, isoprenyl, propargyl, 2-butynyl, $CH_2CN$, 2-chloroethyl, 2-bromoethyl, 2-hydroxyethyl and 2-methoxyethyl.

Two of the radicals $R^5$, $R^6$ and $R^7$ may also, together with the nitrogen atom whose substituents they are, form a heterocyclic ring. Examples of such heterocyclic rings are pyrrolidine, piperidine, 3-methylpiperidine, 4-methylpiperidine, 3,5-dimethylpiperidine, 3,3-dimethylpiperidine, hexamethylenimine, 3,5,5-trimethylhexamethylenimine, morpholine, 2,6-dimethylmorpholine, thiomorpholine, 2,6-dimethylthiomorpholine, 3-hydroxymethylpiperidine, 3-methoxymethylpiperidine, 3-hydroxypiperidine, 4-hydroxypiperidine, 3-methoxypiperidine and 4-methoxypiperidine.

The active ingredients according to the invention may be employed as plant growth regulators.

Plant growth regulators may have several different effects on plants. The action of the compounds depends essentially on the time applied, with reference to the development stage of the seed or plant, on the amount of active ingredient applied to the plants or their habitat, and on the application method employed. At all events, growth regulators are intended to influence crop plants in a desired manner.

Plant growth-regulating compounds may be used for instance to inhibit vegetative plant growth. Such an inhibition of growth is of economic interest inter alia with grass, because suppressed grass growth can, for example, result in a reduction of the mowing frequency in lawns and parks, and on sportsgrounds and roadsides. It is also important to inhibit the growth of herbaceous and woody plants on roadsides and in the vicinity of overhead transmission lines, or quite generally where vigorous growth is undesired.

A further important application area for growth regulators is the inhibition of upward plant growth in cereals; a reduction in stem length reduces or completely eliminates the danger of lodging before the plants are harvested. Growth regulators may also strengthen the stems of cereals, which also counters lodging.

The inhibition of vegetative growth also makes closer planting possible in numerous crops, which means an increase in yield based on the area cropped.

A further mechanism for increasing yields with plant growth regulators is based on the fact that blossom and fruit formation benefits to a greater extent from the nutrients when vegetative growth is restricted.

However, plant growth regulators may also frequently be employed to promote vegetative growth. This is of great use when the vegetative plant parts are harvested. The promotion of vegetative growth may, however, simultaneously result in an increase in generative growth, e.g., the formation of more or bigger fruit.

Increases in yield may also be achieved in many instances by influencing plant metabolism without there being any noticeable change in vegetative growth. Growth regulators may also change the composition of plants and thus improve the quality of the harvested products. It is for example possible to increase the sugar content of sugar beets, sugarcane, pineapples and citruses, or to raise the protein content in soybeans and cereals.

Parthenocarpic fruits may also be formed under the influence of growth regulators. Further, the sex of the flowers may be influenced.

The production or the flow of secondary plant materials may also be positively influenced with growth regulators. The stimulation of latex flow in rubber trees may be mentioned by way of example.

During the growth of the plant, branching may be increased by growth regulators as a result of the chemical control of apical dominance. This is of interest for instance in the propagation of plant cuttings. It is, however, also possible to inhibit the growth of lateral branches, e.g., to prevent sucker growth in tobacco plants after topping, and thus to promote leaf growth.

Growth regulators may also be used to defoliate plants at any desired time. Such a defoliation facilitates mechanical harvesting, e.g., in grapes or cotton, or reduces transpiration at a time when the plant is to be transplanted.

Premature fruit drop may also be prevented by growth regulators. It is, however, also possible to thin out chemically by promoting fruit drop to a certain extent. Growth regulators may also be used to reduce the force to be exerted for plucking off fruit from crop plants at harvest time, making mechanical harvesting possible, or facilitating manual harvesting.

Further, growth regulators may be used to accelerate or delay the ripening of material before or after harvesting. This feature is of particular advantage, because market needs can be optimally accommodated. Growth regulators may also in many cases improve fruit color. It is also possible to concentrate ripening with growth regulators, this making it possible, for example in tobacco, tomatoes or coffee, to harvest completely mechanically or manually in just one operation.

Growth regulators can also influence the dormancy of seeds or buds, i.e., the annual endogenous rhythm; plants such as pineapples or ornamentals in nurseries can thus be made to germinate, sprout or blossom at a time at which they normally show no willingness to do so.

Growth regulators may further be employed to delay budding or seed germination, for example in order in frost-endangered areas to prevent damage by late frosts.

Growth regulators may also make crop plants halophilic, i.e., they may be cultivated in salty soils.

Growth regulators can also make plants more frost- and drought-resistant.

The novel α-ammonium acetanilides of the formula I may be prepared in accordance with the following scheme:

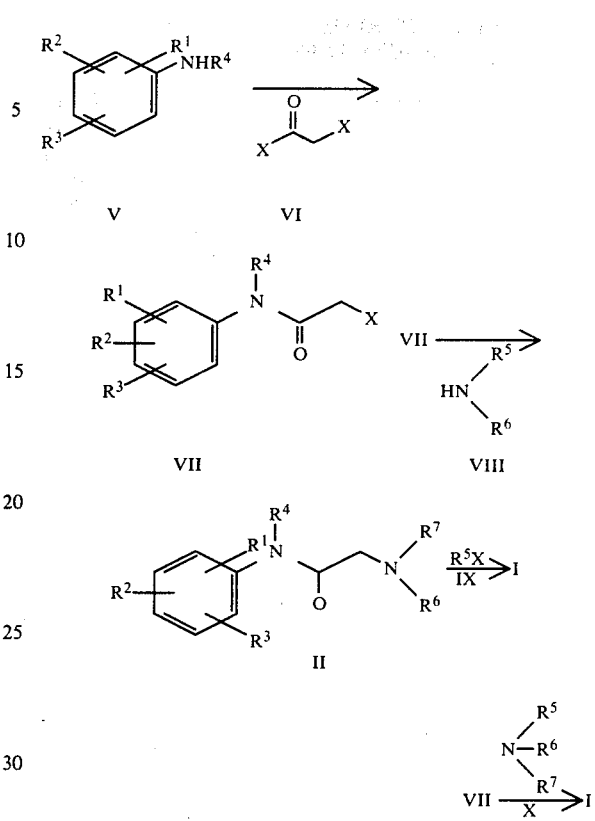

X = halogen.

A secondary aniline of the formula V is reacted with an α-halocarboxylic acid halide of the formula VI to give an α-halocarboxanilide VII (see, for example, Houben-Weyl, 11/2, p.35). The α-halocarboxanilides VII are reacted with secondary amines VIII to give α-aminoacetanilides II, which are subsequently quaternized with alkylating agents IX to the compounds I according to the invention. Alternatively, the ammonium salts I may also be manufactured direct from the α-halocarboxanilides VII and tertiary amines X.

Examples of anilines of the formula V are N-methylaniline, N-ethylaniline, N-propylaniline, 4-chloro-N-methylaniline, 2,4-chloro-N-methylaniline, 4-chloro-2,N-dimethylaniline, N-allyl-4-chloro-2-methylaniline, 4-chloro-N-ethyl-2-methylaniline, 4-chloro-2-methyl-N-propylaniline, 4-chloro-2-methyl-N-propargylaniline, N-methyl-3-trifluoromethylaniline, 3-chloro-4-fluoro-N-methylaniline, 3,4-difluoro-N-methylaniline, 3-methoxy-N-methylaniline, N-methyl-3-nitroaniline, 3-ethyl-5,N-dimethylaniline, 3-isopropyl-N-methylaniline, 4-fluoro-3,N-dimethylaniline, 2,4-difluoro-N-methylaniline, 4-fluoro-3,N-dimethylaniline, and 3-chloro-N-methylaniline.

Examples of halocarboxylic acid halides of the formula VI are α-chloroacetyl chloride and α-bromoacetyl bromide.

Examples of quaternary amines of the formula VIII are pyrrolidine, piperidine, hexamethylenimine, morpholine, 3,5-dimethylmorpholine, thiamorpholine, diethylamine, dipropylamine, diallylamine, 1,2,3,6-tetrahydropyrimidine, 3-hydroxypiperidine, 3-hydroxymethylenepiperidine, 3,5-dimethylpiperidine, 3-methylpiperidine, 4-methylpiperidine, 4-hydroxypiperidine, 2,6-dimethylmorpholine and 2,6-dimethylthiomorpholine.

Examples of quaternizing agents of the formula IX are methyl bromide, bromoethane, bromopropane, bromobutane, 3-methylbromobutane, allyl bromide, crotyl bromide and propargyl bromide.

Examples of tertiary amines of the formula X are N-methylpyrrolidine, N-ethylpyrrolidine, N-propylpyrrolidine, N-methylpiperidine, N-ethylpiperidine, N-propylpiperidine and N-methylmorpholine.

A compound of the formula IX is reacted for example at a temperature of from 10° to 150° C. in the presence or absence of a solvent, e.g., ethanol, methanol, chloroform, methylene chloride, acetonitrile, dimethylformamide or ethyl acetate, at atmospheric or superatmospheric pressure.

Preferably, compound IX is employed in a 10 to 100% excess of the stoichiometric amount, based on compound II.

The reaction of a compound of the formula VII with a compound of the formula X is carried out for instance at from 10° to 150° C. in the presence or absence of a solvent, e.g., ethanol, methanol, chloroform, methylene chloride, acetonitrile, dimethylformamide or ethyl acetate, at atmospheric or superatmospheric pressure.

The starting materials are reacted in stoichiometric amounts, or compound X is employed in a 10 to 100% excess of the stiochiometric amount, based on compound VII.

The following recipes and examples illustrate the manufacture of the active ingredients of the formula I according to the invention and their precursors. Recipe A for the synthesis of halocarboxanilides of the formula VII N-chloroacetyl-N-methyl-4-chloro-2-methylaniline (A0)

44 g of sodium acetate in 200 ml of water is added to a solution of 60 g of N-methyl-4-chloro-2-methylaniline in 150 ml of acetone. Subsequently, 56 g of chloroacetyl chloride is dripped in over a period of 3 hours, the temperature being kept at less than 35° C. After the mixture has been stirred for 2 hours at room temperature, 200 ml of ice water is added. The mixture is then cooled to 5° to 10° C. and filtered, and the filter cake is washed with water and dried in vacuo at 60° C. Yield: 85 g. Melting point: 85°–87° C. Recipe B for the synthesis of α-aminoacetanilides of the formula II N-pyrrolidinoacetyl-N-methyl-4-chloro-2-methylaniline (A1)

42.6 g of pyrrolidine is dripped into a solution of 46.4 g of the compound A0 in 300 ml of ethanol. The reaction temperature is kept at less than 40° C. The mixture is stirred for 3 hours at room temperature, the ethanol is evaporated, the residue is dissolved in ether/water, the aqueous phase is extracted several times with ether, the combined organic phases are washed with water and dried over $Na_2SO_4$, and ether is evaporated off. The product crystallizes after trituration with n-pentane. Yield: 46 g. Melting point: 59° C.

The α-aminoacetanilides of secondary amines listed in the following 2 tables may be prepared analogously.

| No. | $R^1$ | $R^2$ | $R^3$ | $R^4$ | $R^5$ | $R^6$ | m.p. |
|---|---|---|---|---|---|---|---|
| A1 | 2-$CH_3$ | 4-Cl | H | $CH_3$ | $(CH_2)_4$ | | 59° C. |
| A2 | 2-$CH_3$ | 4-Cl | H | $CH_3$ | $(CH_2)_5$ | | oil |
| A3 | 3-$CF_3$ | H | H | $CH_3$ | $(CH_2)_4$ | | |
| A4 | 4-F | 3-Cl | H | $CH_3$ | $(CH_2)_4$ | | |
| A5 | 3-$CH_3$ | H | H | $CH_3$ | $(CH_2)_5$ | | |
| A6 | 2-F | 4-F | H | $CH_3$ | $(CH_2)_4$ | | |
| A7 | 3-$OCH_3$ | H | H | $CH_3$ | $(CH_2)_4$ | | |
| A8 | 3-$NO_2$ | H | H | $CH_3$ | $(CH_2)_4$ | | |
| A9 | 3-$C_2H_5$ | 5-$CH_3$ | H | $CH_3$ | $(CH_2)_4$ | | |
| A10 | 3-i-Prop | H | H | $CH_3$ | $(CH_2)_4$ | | |
| A11 | 3-$CH_3$ | 4-F | H | $CH_3$ | $(CH_2)_4$ | | |
| A12 | 4-Cl | H | H | $CH_3$ | $(CH_2)_4$ | | |
| A13 | 3-$C_2H_5$ | 5-$CH_3$ | H | $CH_3$ | $(CH_2)_5$ | | |
| A14 | 3-$C_2H_5$ | 5-$CH_3$ | H | $CH_3$ | $(CH_2)_6$ | | |
| A15 | 3-$OCH_3$ | H | H | $CH_3$ | $(CH_2)_5$ | | |
| A16 | 2-F | 4-F | H | $CH_3$ | $(CH_2)_5$ | | |
| A17 | 4-Cl | H | H | $CH_3$ | $(CH_2)_5$ | | |
| A18 | 3-$NO_2$ | H | H | $CH_3$ | $(CH_2)_5$ | | |
| A19 | 3-$CH_3$ | 4-F | H | $CH_3$ | $(CH_2)_5$ | | |
| A20 | 3-i-Prop | H | H | $CH_3$ | $(CH_2)_5$ | | |
| A21 | 2-$CH_3$ | 4-Cl | H | $CH_3$ | $(CH_2)_6$ | | |
| A22 | 2-$CH_3$ | 4-Cl | H | $CH_3$ | $CH_2CHCH_3(CH_2)_3$ | | |
| A23 | 2-$CH_3$ | 4-Cl | H | $CH_3$ | Propyl | Propyl | |
| A24 | 4-F | 3-$CH_3$ | H | $CH_3$ | $(CH_2)_6$ | | |
| A25 | 2-$CH_3$ | 4-Cl | H | Allyl | $(CH_2)_4$ | | |
| A26 | 2-$CH_3$ | 4-Cl | H | $CH_3$ | Ethyl | Ethyl | |
| A27 | 2-$CH_3$ | 4-Cl | H | $CH_3$ | $[(CH_2)_2]_2O$ | | |
| A28 | 2-$CH_3$ | 4-Cl | H | $CH_3$ | $(CH_2CHCH_3)_2O$ | | |
| A29 | 4-Br | H | H | $CH_3$ | $(CH_2)_4$ | | |
| A30 | H | H | H | $CH_3$ | $(CH_2)_4$ | | |
| A31 | 2-Cl | 4-Cl | 6-Cl | $CH_3$ | $(CH_2)_4$ | | |
| A32 | 2-Cl | 3-Cl | 4-Cl | $CH_3$ | $(CH_2)_4$ | | |
| A33 | 2-$CH_3$ | 4-Cl | 5-Cl | $CH_3$ | $(CH_2)_4$ | | |

-continued

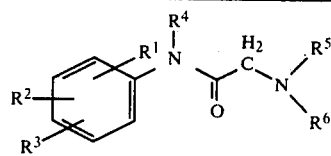

| No. | R¹ | R² | R³ | R⁴ | R⁵ | R⁶ | m.p. |
|-----|-----|-----|-----|-----|-----|-----|------|
| A34 | 2-CH₃ | 4-Cl | H | C₂H₅ | | (CH₂)₄ | |
| A35 | 2-CH₃ | 4-Cl | H | n-Propyl | | (CH₂)₄ | |
| A36 | 2-CH₃ | 4-Cl | H | Propargyl | | (CH₂)₄ | |
| A37 | 2-CH₃ | 4-Cl | H | Isopropyl | | (CH₂)₄ | |

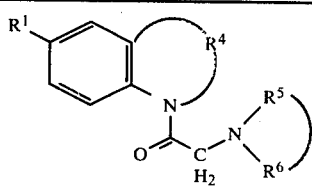

| No. | R¹ | R⁵ | R⁶ | R⁴ |
|-----|-----|-----|-----|-----|
| A38 | H | (CH₂)₄ | | (CH₂)₂ |
| A39 | H | (CH₂)₅ | | (CH₂)₂ |
| A40 | H | (CH₂)₄ | | (CH₂)₃ |
| A41 | H | (CH₂)₅ | | (CH₂)₃ |
| A42 | Cl | (CH₂)₄ | | (CH₂)₂ |
| A43 | Cl | (CH₂)₄ | | (CH₂)₃ |
| A44 | Br | (CH₂)₄ | | (CH₂)₂ |
| A45 | Br | (CH₂)₄ | | (CH₂)₃ |

EXAMPLE 1

N-[2-(4-chloro-2-methyl-N-methylanilino)-2-oxo]-ethyl-N-allylpyrrolidinium bromide A solution of 46 g of compound A1 and 42 g of 1-bromopropene-2 in 200 ml of ethyl acetate is refluxed for 4 hours. After the mixture has cooled, the precipitated product is filtered off, washed with ethyl acetate and dried.

Yield: 62 g; melting point: 173°-175° C.

EXAMPLE 2

N-[2-(4-chloro-2-methyl-N-methylanilino)-2-oxo]-ethyl-N-ethylpyrrolidinium bromide A solution of 20 g of compound A1 and 15.9 g of ethyl bromide in 200 ml of acetonitrile is stirred for 14 hours at room temperature, and then concentrated. The crystalline residue is triturated with ether, filtered and dried.

Yield: 25 g; melting point: 179°-181° C.

EXAMPLE 3

N-[2-(4-chloro-2-methyl-N-methylanilino)-2-oxo]-ethyl-N-methylpiperidinium chloride 40 g of N-methylpiperidine is dripped into a solution of 46.4 g of compound A0 in 150 ml of acetonitrile, the reaction temperature being kept at less than 25° C. After 14 hours, the precipitated product is washed with ether and dried.

Yield: 52 g; melting point: above 230° C.

EXAMPLE 4

N-[2-(4-chloro-2-methyl-N-methylanilino)-2-oxo]-ethyl-N-methylpyrrolidinium bromide A solution of 21 g of bromomethane and 30 g of compound A1 in 300 ml of acetonitrile is stirred for 14 hours at room temperature. The product which crystallizes out is filtered, washed with ether and dried.

Yield: 37 g; melting point: 157° C.

The compounds according to the invention listed in the following tables may be prepared analogously.

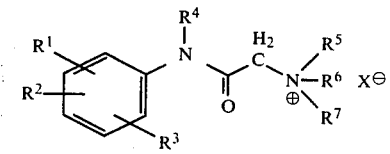

| No. | R¹ | R² | R³ | R⁴ | R⁵ | R⁶ | R⁷ | X | m.p. °C. Z = decomposition |
|-----|-----|-----|-----|-----|-----|-----|-----|-----|-----|
| 1 | 2-CH₃ | 4-Cl | H | CH₃ | Allyl | (CH₂)₄ | | Br | 173-175 Z |
| 2 | 2-CH₃ | 4-Cl | H | CH₃ | Allyl | (CH₂)₅ | | Br | resin |
| 3 | 3-CF₃ | H | H | CH₃ | Allyl | (CH₂)₄ | | Br | resin |
| 4 | 4-F | 3-Cl | H | CH₃ | Allyl | (CH₂)₄ | | Br | 124-126 |
| 5 | 3-CF₃ | H | H | CH₃ | Allyl | (CH₂)₅ | | Br | resin |
| 6 | 2-F | 4-F | H | CH₃ | Allyl | (CH₂)₄ | | Br | 172 |
| 7 | 3-OCH₃ | H | H | CH₃ | Alkyl | (CH₂)₄ | | Br | 145-147 Z |
| 8 | 3-NO₂ | H | H | CH₃ | Allyl | (CH₂)₄ | | Br | 128-130 |
| 9 | 3-C₂H₅ | 5-CH₃ | H | CH₃ | Allyl | (CH₂)₄ | | Br | 135-136 |
| 10 | 3-i-Prop | H | H | CH₃ | Allyl | (CH₂)₄ | | Br | resin |
| 11 | 3-CH₃ | 4-F | H | CH₃ | Allyl | (CH₂)₄ | | Br | resin |

-continued

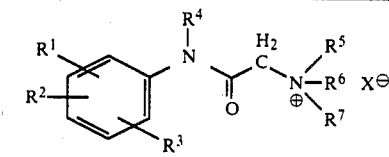

| No. | R¹ | R² | R³ | R⁴ | R⁵ | R⁶ ⟅ R⁷ | | X | m.p. °C. Z = decomposition |
|---|---|---|---|---|---|---|---|---|---|
| 12 | 4-Cl | H | H | $CH_3$ | Allyl | $(CH_2)_4$ | | Br | 100–103 |
| 13 | 3-$C_2H_5$ | 5-$CH_3$ | H | $CH_3$ | Allyl | $(CH_2)_5$ | | Br | 123–125 |
| 14 | 3-$C_2H_5$ | 5-$CH_3$ | H | $CH_3$ | Allyl | $(CH_2)_6$ | | Br | 90–92 |
| 15 | 3-$OCH_3$ | H | H | $CH_3$ | Allyl | $(CH_2)_5$ | | Br | 109–110 |
| 16 | 2-F | 4-F | H | $CH_3$ | Allyl | $(CH_2)_5$ | | Br | 182 |
| 17 | 4-Cl | H | H | $CH_3$ | Allyl | $(CH_2)_5$ | | Br | 144–146 |
| 18 | 3-$NO_2$ | H | H | $CH_3$ | Allyl | $(CH_2)_5$ | | Br | 170–172 Z |
| 19 | 3-$CH_3$ | 4-F | H | $CH_3$ | Allyl | $(CH_2)_5$ | | Br | 96–101 |
| 20 | 3-i-Prop | H | H | $CH_3$ | Allyl | $(CH_2)_5$ | | Br | resin |
| 21 | 2-$CH_3$ | 4-Cl | H | $CH_3$ | Allyl | $(CH_2)_6$ | | Br | 91–98 |
| 22 | 2-$CH_3$ | 4-Cl | H | $CH_3$ | Crotyl | $(CH_2)_4$ | | Br | 171–175 Z |
| 23 | 2-$CH_3$ | 4-Cl | H | $CH_3$ | Allyl | $CH_2CHCH_3(CH_2)_3$ | | Br | 84–85 |
| 24 | 2-$CH_3$ | 4-Cl | H | $CH_3$ | Allyl | Propyl | Propyl | Br | |
| 25 | 2-$CH_3$ | 4-Cl | H | $CH_3$ | Propargyl | $(CH_2)_4$ | | Br | 175–178 Z |
| 26 | 2-$CH_3$ | 4-Cl | H | $CH_3$ | $CH_3$ | $(CH_2)_4$ | | Br | 157 Z |
| 27 | 4-F | 3-$CH_3$ | H | $CH_3$ | Allyl | $(CH_2)_6$ | | Br | 180 Z |
| 28 | 2-$CH_3$ | 4-Cl | H | Allyl | Allyl | $(CH_2)_4$ | | Br | resin |
| 29 | 2-$CH_3$ | 4-Cl | H | $CH_3$ | Ethyl | $(CH_2)_4$ | | Br | 179–181 |
| 30 | 2-$CH_3$ | 4-Cl | H | $CH_3$ | Propyl | $(CH_2)_4$ | | Br | 208–210 |
| 31 | 2-$CH_3$ | 4-Cl | H | $CH_3$ | Butyl | $(CH_2)_4$ | | Br | 170–172 |
| 32 | 2-$CH_3$ | 4-Cl | H | $CH_3$ | Ethyl | Ethyl | Ethyl | Cl | |
| 33 | 2-$CH_3$ | 4-Cl | H | $CH_3$ | $CH_3$ | $[(CH_2)_2]_2O$ | | Cl | 210–211 Z |
| 34 | 2-$CH_3$ | 4-Cl | H | $CH_3$ | Allyl | $[(CH_2)_2]_2O$ | | Br | 166–168 Z |
| 35 | 2-$CH_3$ | 4-Cl | H | $CH_3$ | Allyl | $(CH_2CHCH_3)_2O$ | | Br | 168–169 Z |
| 36 | 2-$CH_3$ | 4-Cl | H | $CH_3$ | Allyl | $CH_2CHOH(CH_2)_3$ | | Br | 81–83 |
| 37 | 2-$CH_3$ | 4-Cl | H | $CH_3$ | Allyl | $CH_2CH=CH(CH_2)_2$ | | Br | 148–149 Z |
| 38 | 2-$CH_3$ | 4-Cl | H | $CH_3$ | Allyl | $CH_2CHCH_2OH(CH_2)_3$ | | Br | 86–88 |
| 39 | 2-$CH_3$ | 4-Cl | H | $C_2H_5$ | Allyl | $(CH_2)_4$ | | Br | 50 |
| 40 | 2-$CH_3$ | 4-Cl | H | n-$C_3H_7$ | Allyl | $(CH_2)_4$ | | Br | |
| 41 | 2-$CH_3$ | 4-Cl | H | i-$C_3H_7$ | Allyl | $(CH_2)_4$ | | Br | |
| 42 | 2-$CH_3$ | 4-Cl | H | Propargyl | Allyl | $(CH_2)_4$ | | Br | resin |
| 43 | 2-$CH_3$ | 4-Cl | H | $CH_3$ | $(CH_2)_2CH(CH_3)_2$ | $(CH_2)_4$ | | Br | 168–169 Z |
| 44 | 2-$CH_3$ | 4-Cl | H | $CH_3$ | $CH_3$ | $(CH_2)_5$ | | Cl | 230 |
| 45 | 2-$CH_3$ | 4-Cl | H | $CH_3$ | Allyl | $(CH_2)_4$ | | $CH_3OSO_3^\ominus$ | |
| 46 | 2-$CH_3$ | 4-Cl | H | $CH_3$ | $CH_3$ | $(CH_2)_4$ | | $CF_3SO_3^\ominus$ | |
| 47 | 2-Cl | 4-Cl | 6-Cl | $CH_3$ | Allyl | $(CH_2)_4$ | | Br | |
| 48 | 2-Cl | 3-Cl | 4-Cl | $CH_3$ | Allyl | $(CH_2)_4$ | | Br | |
| 49 | 2-$CH_3$ | 4-Cl | 5-Cl | $CH_3$ | Allyl | $(CH_2)_4$ | | Br | |
| 50 | 2-$CH_3$ | 4-Cl | H | $C_2H_5$ | $CH_3$ | $(CH_2)_4$ | | Br | 60 |
| 51 | 2-$CH_3$ | 4-Cl | H | $C_2H_5$ | $CH_3$ | $(CH_2)_5$ | | Br | 88–89 |
| 52 | 2-$CH_3$ | 4-Cl | H | $C_2H_5$ | Allyl | $(CH_2)_5$ | | Br | 88–90 |
| 53 | 2-$CH_3$ | 4-Cl | H | $CH_2C_6H_5$ | Allyl | $(CH_2)_4$ | | Br | |
| 54 | H | H | H | $CH_3$ | Allyl | $(CH_2)_4$ | | Br | 136 Z |
| 55 | 3-Cl | H | H | $CH_3$ | Allyl | $(CH_2)_4$ | | Br | 134 Z |
| 56 | 3-Cl | H | H | $CH_3$ | $CH_3$ | $(CH_2)_4$ | | Br | 123 Z |
| 57 | H | H | H | $CH_3$ | $CH_3$ | $(CH_2)_4$ | | Br | 130 Z |
| 58 | H | H | H | $CH_3$ | $C_2H_5$ | $(CH_2)_4$ | | Br | 57 |
| 59 | 3-Cl | H | H | $CH_3$ | $C_2H_5$ | $(CH_2)_4$ | | Br | 129 Z |

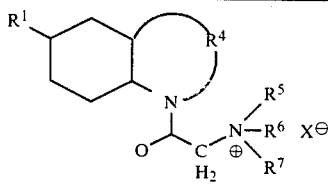

| No. | R¹ | R⁵ | R⁶ | R⁷ | R⁴ | X | m.p. °C |
|---|---|---|---|---|---|---|---|
| 60 | H | $(CH_2)_4$ | Allyl | $(CH_2)_2$ | Br | | 178 Z. |
| 61 | H | $(CH_2)_4$ | Allyl | $(CH_2)_3$ | Br | | 160 Z. |
| 62 | H | $(CH_2)_5$ | Allyl | $(CH_2)_3$ | Br | | resin |
| 63 | H | $(CH_2)_5$ | Allyl | $(CH_2)_2$ | Br | | |
| 64 | Cl | $(CH_2)_4$ | Allyl | $(CH_2)_2$ | Br | | |
| 65 | Cl | $(CH_2)_4$ | Allyl | $(CH_2)_3$ | Br | | |
| 66 | Br | $(CH_2)_4$ | Allyl | $(CH_2)_2$ | Br | | |

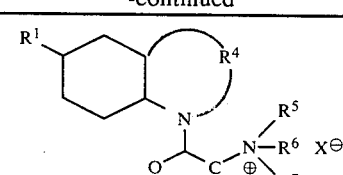

| No. | R¹ | R⁵ | R⁶ | R⁷ | R⁴ | X | m.p. °C |
|---|---|---|---|---|---|---|---|
| 67 | Br | $(CH_2)_4$ | Allyl | $(CH_2)_3$ | Br | | |

The growth-regulating agents contain from 0.1 to 95% (wt%) of active ingredient, preferably from 0.5 to 90%. The application rates depend on the effect desired, and range from 0.001 to 3 kg and more, but preferably from 0.01 to 1 kg of active ingredient per hectare.

Application may be effected for instance in the form of directly sprayable solutions, powders, suspensions, dispersions, emulsions, oil dispersions, pastes, dusts, broadcasting agents, or granules. The forms of application depend entirely on the purpose for which the agents are being used; in any case they should ensure as fine a distribution of the active ingredient as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated caster oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

Application is effected by treating the plants, seed or the soil with the agents, for example spraying, atomizing, dusting, disinfecting or impregnating.

The agents according to the invention may, in these application forms, also be mixed and applied with other active ingredients, e.g., herbicides, insecticides, other growth regulators, bactericides, fungicides and fertilizers. When mixed with other growth regulators, the spectrum of action is in many cases increased; with a number of these compositions, synergistic effects also occur; i.e., the action of the combination product is greater than the effect of the individual components added together.

The following examples illustrate the action of the compounds to be used in accordance with the invention as plant growth regulators, without restricting the invention to these uses.

The above agents may be added to the active ingredients according to the invention in a weight ratio of from 1:10 to 10:1. If desired, they need not be added until immediately before use (tankmix).

EXAMPLE 5

Action on Sunflowers

In the greenhouse, sunflowers were sown, in plastic dishes 11.5 cm in diameter, in a peat culture substrate provided with sufficient nutrients. The active ingredients were sprayed onto the leaves at different application rates, and at a height of the plants of 12 cm.

During the growth period of 23 days, the upward growth of the treated plants was significantly less than that of the untreated control plants, a fact which was confirmed by length measurements at the end of the experiment. 14 plants were measured from each series treated.

The prior art active ingredient CCC (2-chloroethyltrimethylammonium chloride) was used for comparison purposes. The individual figures are given in the following table.

| Influence on the growth height of sunflowers; leaf treatment | | | |
|---|---|---|---|
| | Appln. rate | Plant height | |
| Active ingredient | kg/ha | cm | rel. |
| Control | — | 26.8 | 100 |
| CCC (prior art) | 1.5 | 23.0 | 85.8 |
| 1 | 0.5 | 17.5 | 65.3 |
| | 1.0 | 17.0 | 63.4 |
| | 1.5 | 17.0 | 63.4 |

EXAMPLE 6

Action on Soybeans

In similar manner to Example 5, an experiment was run in small containers in the greenhouse with soybeans. The following results were ascertained after a growth period of 36 days.

| Influence on the growth height of soybeans; leaf treatment | | | |
|---|---|---|---|
| | Appln. rate | Plant height | |
| Active ingredient | kg/ha | cm | rel. |
| Control | — | 28.0 | 100 |
| CCC (prior art) | 1.5 | 27.0 | 96.4 |
| | 6.0 | 26.5 | 94.6 |
| 1 | 1.5 | 10.5 | 37.5 |
| | 6.0 | 10.5 | 37.5 |

EXAMPLE 7

Action on Soybeans; Vessel Experiment

In order to observe the growth of soybeans over a fairly long vegetation period, an experiment was set up using a sandy loam in relatively large vessels. As fertilizer, 0.5 g of N as ammonium nitrate and 0.5 g of $P_2O_5$ as sec-potassium phosphate were added. The plants were grown in a fully conditioned greenhouse chamber under optimum growth conditions. The active ingredients were sprayed at a growth height of 20 cm. During the 2 months of the experiment, in which the control series reached a height of about 60 cm, the growth height of the treated plants was up to 56% less; furthermore; the plants were conspicuous for their very compact habit and very dark green color. The results obtained are given below.

| Influence on growth height of soybeans in conditioned chamber | | | |
|---|---|---|---|
| | Appln. Rate | Plant height | |
| Active ingredient | kg/ha | cm | rel. |
| Control | — | 58.6 | 100 |
| CCC (prior art) | 0.5 | 60.0 | 102.4 |
| | 1.0 | 59.0 | 100.7 |
| | 1.5 | 58.0 | 99.0 |
| 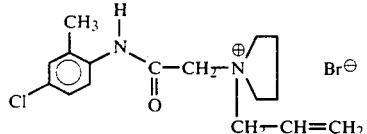 | 0.5 | 41.0 | 70.0 |
| | 1.0 | 30.0 | 51.2 |
| | 1.5 | 29.0 | 49.5 |
| (German Laid-Open Application DE-OS 2,657,728) | | | |
| 1 | 0.5 | 34.5 | 58.9 |
| | 1.0 | 28.5 | 48.6 |
| | 1.5 | 25.5 | 43.5 |

EXAMPLE 8

90 parts by weight of compound 1 is mixed with 20 parts by weight of water. A mixture is obtained which is suitable for application in the form of very fine drops.

EXAMPLE 9

20 parts by weight of compound 2 is dissolved in a mixture consisting of 80 parts by weight of xylene, 10 parts by weight of the adduct of 8 to 10 moles of ethylene oxide with 1 mole of oleic acid-N-monoethanolamide, 5 parts by weight of the calcium salt of dodecylbenzenesulfonic acid, and 5 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

EXAMPLE 10

20 parts by weight of compound 1 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

EXAMPLE 11

20 parts by weight of compound 2 is well mixed with 3 parts by weight of the sodium salt of diisobutylnaphthalene-α-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

EXAMPLE 12

3 parts by weight of compound 3 is intimately mixed with 97 parts by weight of particulate kaolin. A dust is obtained containing 3% by weight of the active ingredient.

EXAMPLE 13

30 parts by weight of compound 4 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE 14

40 parts by weight of compound 1 is intimately mixed with 10 parts of the sodium salt of a phenolsulfonic acid-urea-formaldehyde condensate, 2 parts of silica gel and 48 parts of water to give a stable, aqueous dispersion. Dilution in 100,000 parts by weight of water gives an aqueous dispersion containing 0.04 wt% of active ingredient.

EXAMPLE 15

20 parts of compound 2 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

We claim:

1. A salt of an α-aminoacetanilide of the formula

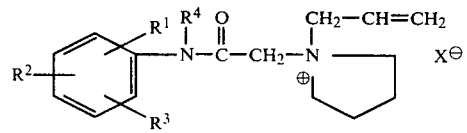

wherein
R' is hydrogen, $C_{1-3}$ alkyl, trifluoromethyl, nitro, chlorine or fluorine,
$R^2$ is hydrogen, methyl, chlorine or fluorine,
$R^3$ is hydrogen or chlorine,
$R^4$ is $C_{1-3}$ alkyl, and
X is chlorine, bromine, nitro, $CH_3OSO_3^{\ominus}$ or $CF_3SO_3^{\ominus}$.

2. N-[2-(4-chloro-2-methyl-N-methylanilino)-2-oxo]-ethyl-N-allylpyrrolidinium bromide.

* * * * *